United States Patent [19]

Müller et al.

[11] Patent Number: 4,771,048
[45] Date of Patent: Sep. 13, 1988

[54] USE OF THIADIAZINONES FOR COMBATING ENDOPARASITES

[75] Inventors: Nikolaus Müller, Monheim; Peter Andrews, Wuppertal, both of Fed. Rep. of Germany

[73] Assignee: Bayer Aktiengesellschaft, Leverkusen, Fed. Rep. of Germany

[21] Appl. No.: 66,787

[22] Filed: Jun. 25, 1987

[30] Foreign Application Priority Data

Jul. 12, 1986 [DE] Fed. Rep. of Germany ....... 3623532

[51] Int. Cl.$^4$ ..................... A61K 31/54; C07D 285/16
[52] U.S. Cl. ........................................ 514/222.5; 544/8
[58] Field of Search ............................ 544/8; 514/222

[56] References Cited

U.S. PATENT DOCUMENTS 4,496,563  1/1985  Acker ....................................... 544/8
4,514,742  10/1985  Schmitt et al. .......................... 544/8

FOREIGN PATENT DOCUMENTS 2742546  3/1978  Fed. Rep. of Germany .......... 544/8

OTHER PUBLICATIONS

Chemical Abstracts, vol. 91, Abstract No. 39541f, Jul. 30, 1979, p. 641.

*Primary Examiner*—John M. Ford
*Assistant Examiner*—Zinna Northington

*Attorney, Agent, or Firm*—Sprung Horn Kramer & Woods

[57] ABSTRACT

The present invention relates to the use of thiadiazinones of the formula I

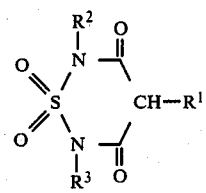

in which
R represents the radical of the formula

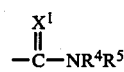

wherein
$X^1$ represents O or S,
$R^4$ represents hydrogen or alkyl,
$R^5$ represents optionally substituted phenyl,
$R^2$ represents hydrogen, alkyl, cycloalkyl, aryl or aralkyl for combating endoparasites in veterinary medicine and to new thiadiazinones of the formula I and the preparation thereof.

6 Claims, No Drawings

USE OF THIADIAZINONES FOR COMBATING ENDOPARASITES

The present invention relates to the use of thiadiazinones for combating endoparasites in veterinary medicine.

The use of thiadiazinones as fungicides on plants has already been disclosed (DE-OS No. (German Published Specification) 3,230,923). However, nothing on their suitability for combating endoparasites, in particular helminths, has been disclosed.

1. It has been found that thiadiazinones of the formula I

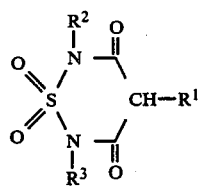

in which
  $R^1$ represents the radical of the formula

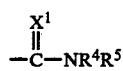

wherein
  $X^1$ represents O or S,
  $R^4$ represents hydrogen or alkyl,
  $R^5$ represents optionally substituted phenyl,
  $R^2$ represents hydrogen, alkyl, cycloalkyl, aryl or aralkyl and
  $R^3$ represents hydrogen, alkyl, cycloalkyl, aryl or aralkyl,
are outstandingly suitable for combating endoparasites in veterinary medicine.

The compounds of the formula I can be present in the form of their various tautomers (keto/enol) and in the form of mixtures of these tautomers, as well as in the form of their salts with bases.

The compounds of the formula I are known or can be prepared by a process analogous to one of the known processes described below.

2. Thiadiazinones of the formula II

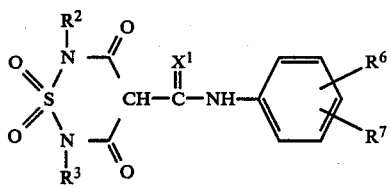

in which
  $R^2$, $R^3$ and $X^1$ have the abovementioned meaning,
  $R^6$ represents $SCF_3$, optionally substituted phenoxy or pyridyloxym, and
  $R^7$ represents hydrogen or halogen, in particular chlorine,
are new.

3. Thiadiazinones of the formula II

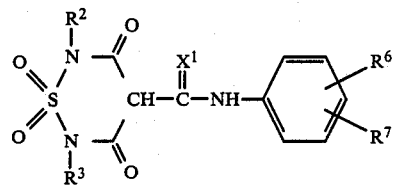

in which
  $R^2$, $R^3$ and $X^1$ have the abovementioned meaning,
  $R^6$ represents $SCF_3$, optionally substituted phenoxy or pyridyloxy, and
  $R^7$ represents hydrogen or halogen, in particular chlorine,
are prepared by a process in which
(a) thiadiazinones of the formula III

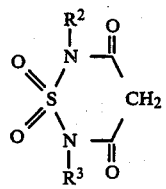

in which
  $R^2$ and $R^3$ have the abovementioned meaning, are reacted with isocyanates of the formula IV

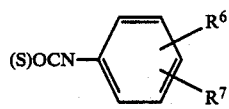

in which
  $R^6$ and $R^7$ have the abovementioned meaning, if appropriate in the presence of catalysts, or by a process in which
(b) thiadiazinones of the formula V

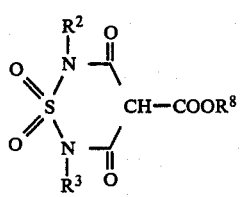

in which
  $R^2$ and $R^3$ have the abovementioned meaning and
  $R^8$ represents $C_{1-4}$-alkyl, are reacted with amines of the formula V

in which
  $R^4$ and $R^5$ have the abovementioned meaning.

Preferred compounds of the formula I are those in which
  $R^2$ represents hydrogen, $C_1-C_4$-alkyl, $C_{3-8}$-cycloalkyl, phenyl or benzyl, which can optionally be substituted,
  $R^3$ represents hydrogen, $C_1-C_4$-alkyl, $C_{3-8}$-cycloalkyl, phenyl or benzyl, which can optionally be substituted, $R^1$ represents the radical —CO—NR$^4$R$^5$,
$R^4$ represents hydrogen or C$_{1-4}$-alkyl and
$R^5$ represents phenyl, which optionally carries one or more identical or different substituents from the following group: alkyl with preferably 1 to 4, in particular 1 or 2, carbon atoms, such as methyl, ethyl, n- and i-propyl and n-, i- and t-butyl; alkoxy with preferably 1 to 4, in particular 1 or 2, carbon atoms, such as methoxy, ethoxy, n- and i-propyloxy and n-, i- and t-butyloxy; alkylthio with preferably 1 to 4, in particular 1 or 2, carbon atoms, such as methylthio, ethylthio, n- and i-propylthio and n-, i- and t-butylthio; halogenoalkyl with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethyl or fluoro- or chloroethyl; halogenoalkoxy with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethoxy; halogenoalkylthio with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethylthio; alkylenedioxy with preferably 1 or 2 carbon atoms, such as methylenedioxy or ethylenedioxy; halogen-substituted alkylenedioxy with preferably 1 or 2 carbon atoms and preferably 1 to 4, in particular 2 or 3, halogen atoms, the halogen atoms being identical or different and halogen atoms being, preferably, fluorine or chlorine, in particular fluorine, such as difluoromethylenedioxy, trifluoroethylenedioxy or tetrafluoroethylenedioxy; hydroxyl; halogen, preferably fluorine, chlorine, bromine and iodine, in particular chlorine and bromine; cyano; nitro; amino; monoalkyl- and dialkylamino with preferably 1 to 4, in particular 1 or 2, carbon atoms per alkyl group, such as methylamino, methyl-ethyl-amino, n- and i-propylamino and methy-n-butylamino; formyl; carboxyl; carbalkoxy with preferably 2 to 4, in particular 2 or 3, carbon atoms, such as carbomethoxy or carboethoxy; sulpho (—SO$_3$H); alkylsulphonyl with preferably 1 to 4, in particular 1 or 2, carbon atoms, such as methylsulphonyl or ethylsulphonyl; arylsulphonyl with preferably 6 or 10 aryl-carbon atoms, such as phenylsulphonyl; phenyl, naphthyl, phenoxy, naphthoxy, phenylthio and heteroaryloxy, such as, for example, pyridyloxy, which can in turn be further substituted.

Particularly preferred compounds of the formula I are those
in which
$R^2$ represents C$_1$–C$_4$-alkyl, cyclohexyl, phenyl, which is optionally substituted by halogen, or benzyl,
$R^3$ represents C$_1$–C$_4$-alkyl, cyclohexyl, phenyl, which is optionally substituted by halogen, or benzyl, and
$R^1$ represents the radical

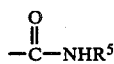

wherein $R^5$ represents phenyl, which is optionally mono-substituted or polysubstituted by identical or different substituents from the group comprising C$_1$–C$_4$-alkyl, in particular methyl, C$_1$–C$_4$-alkoxy, in particular methoxy or ethoxy, C$_1$–C$_4$-halogenoalkoxy, in particular trifluoromethoxy or fluorochloroethoxy, C$_1$–C$_4$-halogenoalkylthio, in particular trifluoromethylthio or fluorochloromethylthio, C$_1$–C$_4$-alkylthio, in particular methylthio, halogenosulphonyl, in particular fluorosulphonyl, chlorosulphonyl, C$_1$–C$_4$-alkylsulphonyl, in particular methylsulphonyl, C$_1$–C$_4$-halogenoalkylsulphonyl, in particular trifluoromethylsulphonyl, C$_1$–C$_4$halogenoalkyl, in particular trifluoromethyl, methylenedioxy or ethylenedioxy, which are optionally substituted by fluorine or chlorine, halogen, in particular fluorine or chlorine, NO$_2$, phenoxy or pyridyloxy, which are optionally substituted by one of the abovementioned radicals.

Especially preferred compounds of the formula I are those
in which
$R^2$ represents C$_1$–C$_4$-alkyl, in particular methyl or ethyl, cyclohexyl, phenyl or chlorophenyl,
$R^3$ represents C$_1$–C$_4$-alkyl, in particular methyl, ethyl, propyl, cyclohexyl or chlorophenyl,
$R^1$ represents the radical —CONHR$^5$ and
$R^5$ represents phenyl which is optionally mono- or polysubstituted by identical or different substituents from the group comprising halogen, in particular chlorine, NO$_2$, CF$_3$, OCF$_3$, SO$_2$F, SCF$_3$, SCF$_2$Cl, SOCF$_3$, SO$_2$CF$_3$, OCH$_3$, OCF$_2$CF$_2$H and phenoxy or pyridyloxy, which are substituted by CF$_3$ or OCF$_3$.

The following compounds of the formula I may be mentioned specifically:

| | | $R^1 = CX^1NR^4R^5$ | | |
| $R^2$ | $R^3$ | $X^1$ | $R^4$ | $R^5$ |
| --- | --- | --- | --- | --- |
| C$_6$H$_5$ | —CH$_3$ | O | H | 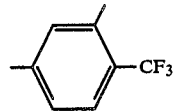 |
| —C$_6$H$_5$ | —CH$_3$ | S | C$_2$H$_5$ | 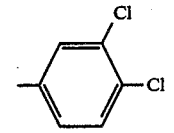 |
| —C$_6$H$_5$ | —CH$_3$ | O | CH$_3$ | 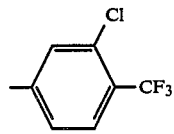 |
| —CH$_3$ | —CH$_3$ | O | H | 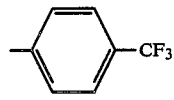 |
| —CH$_3$ | —CH$_3$ | O | CH$_3$ | 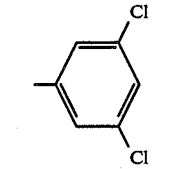 |

As bases with which the compounds of the formula I can form salts there may be mentioned: alkali metal and alkaline earth metal hydroxides, ammonia and primary, secondary and tertiary amines. The following bases may be mentioned as particularly preferred: triethylamine, isopropylamine, t-butylamine, pyridine, α-picoline, trimethylamine, diisopropylamine, morpholine, pyrrolidine and hexamethyleneimine.

Preferred and particularly preferred new compounds of the formula II are those in which the radicals $R^2$ and $R^3$ have the preferred meanings given both the compounds of the in formula I and $X^1$ represents oxygen, $R^6$ represents $SCF_3$, phenoxy or pyridyloxy which is substituted by $CF_3$, $OCF_3$ or $S-CF_3$ and $R^7$ represents hydrogen or chlorine.

The following new compounds of the formula II may be mentioned specifically: 2,6-dimethyl-3,5-dioxo-4[-N-[4-(4-trifluoromethyl(phenoxy)-phenylcarbamoyl]]-2H-3,4,5,6-tetrahydro-1,2,6-thiadiazine 1,1-dioxide, 2-methyl-3,5-dioxo-4-[N-(4-trifluoromethylthiolphenylcarbamoyl]-6-ethyl-2H-3,4,5,6-tetrahydro-1,2,6-thiadiazine 1,1-dioxide, 2-methyl-3,5-dioxo-4-[N-[4-(3-trifluoromethylphenoxy)-phenylcarbamoyl]]-2H-3,4,5,6-tetrahydro-1,2,6-thiadiazine 1,1-dioxide, 2-methyl-3,5-dioxo-4-[N-[4-(4-trifluoromethylphenoxy)-phenylcarbamoyl]]-6-(4-chlorophenyl)-2H-3,4,5,6-tetrahydro-1,2,6-thiadiazine 1,1-dioxide, 2-ethyl-3,5-dioxo-4-[N-[4-trifluoromethylthio]phenylcarbamoyl]-6-cyclohexyl-2H-3,4,5,6-tetrahydro-1,2,6-thiadiazine 1,1-dioxide and 2-methyl-3,5-dioxo-4-[N-[3-chloro-4-trifluoromethylthio]phenylcarbamoyl]-6-phenyl-2H-3,4,5,6-tetrahydro-1,2,6-thiadiazine 1,1-dioxide.

If 1,3-dimethyl-2-thia-1,3-diaza-cyclohexane-4,6-dione is used as the compound of the formula III and p-SCF$_3$-phenylisocyanate is used as the compound of the formula IV in process 3 a for the preparation of the new thiadiazinones of the formula II, the process can be represented by the following equation:

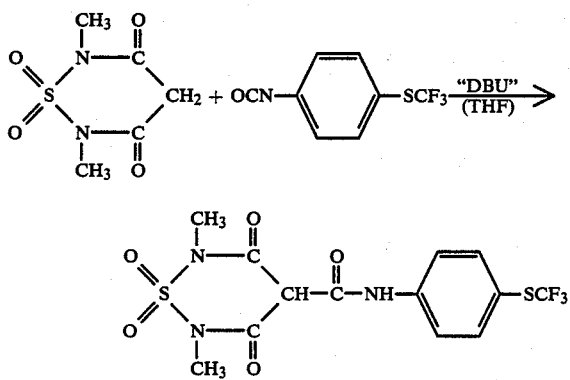

Compounds of the formula III in which the substituents $R^2$ and $R^3$ have the preferred and particularly preferred meanings given in the case of the compounds of the formula I are preferably used. The following compounds of the formula III may be mentioned specifically: 2,6-dimethyl-3,5-dioxo-2H-3,4,5,6-tetrahydro-1,2,6-thiadiazine 1,1-dioxide, 2-methyl-6-isopropyl-3,5-dioxo-2-H-3,4,5,6-tetrahydro-1,2,6-thiadiazine 1,1-dioxide, 2-ethyl-6-cyclohexyl-3,5-dioxo-2-H-3,4,5,6-tetrahydro-1,2,6-thiadiazine 1,1-dioxide, 2-methyl-6-phenyl-3,5-dioxo-2H-3,4,5,6-tetrahydro-1,2,6-thiadiazine 1,1-dioxide and 2-isopropyl-6-(4-chlorophenyl)-3,5-dioxo-2-H-3,4,5,6-tetrahydro-1,2,6-thiadiazine 1,1-dioxide.

The compounds of the formula III are known or they can be prepared by processes analogous to known processes.

Phenyl isocyanates of the formula IV in which the substituents $R^6$ and $R^7$ have the abovementioned preferred meanings are preferably used.

The following phenyl isocyanates of the formula IV may be mentioned specifically: phenyl isocyanate, p-chlorophenyl isocyanate, p-chlorophenyl isothiocyanate, 4-trifluoromethylphenyl isocyanate, 3-chloro-4-trifluoromethyl-phenyl isocyanate, 4-trifluoromethoxyphenyl isocyanate, 4-trifluoromethylthiophenyl isocyanate, 3,4-dichlorophenyl isocyanate, 4-(4-trifluoromethylphenoxy)-phenyl isocyanate, 4-(3-trifluoromethylphenoxy)phenyl isocyanate, 4-(5'-trifluoromethyl-2'-pyridyloxy)-phenyl isocyanate and 3-chloro-4-trifluoromethoxyphenyl isocyanate.

Compounds of the formulae III and IV are reacted in the presence of diluents and in the presence of bases, and if appropriate in the presence of catalysts.

Bases which may be mentioned are: alkali metal and alkaline earth metal alcoholates and tertiary amines. The following bases may be mentioned as particularly preferred: triethylamine, pyridine, picolines, trimethylamine, N-methylmorpholine, N-ethylpyrrolidine, diazabicyclo(4,3,0)undecene (DBU), 1,4-diazo-bicyclo-2,2,2octane (DABCO) and diazabicyclo(3,2,0)nonene (DBN).

Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and moreover ketones, such as acetone, methyl ethyl ketone, methyl isopropyl ketone and methyl isobutyl ketone, and in addition esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethylsulphoxide, tetramethylenesulphone and hexamethylphosphoric acid triamide.

Possible catalysts are the customary catalysts for reactions with isocyanates. Catalysts which may be mentioned are: metal catalysts of Zn, Sn and Pb, such as dibutyltin dilaurate, dibutyltin dioxide, tin octoate, lead octoate, zinc octoate, zinc chloride and zinc acetate.

The reaction is carried out between 0° and 150° C., preferably between 20° and 50° C. The reaction is preferably carried out under normal pressure.

The compounds of the formulae III and IV are employed in equimolar amounts, and a slight excess of one or other of the components provides no substantial advantages.

Working up is effected in a manner which is known per se, for example by adding dilute acid to the reaction mixture and filtering off the product or separating off the organic phase and distilling off the solvent.

If 1-phenyl-2-thia-5-carbethoxy-1,3-diazacyclohexane-4,6-dione is used as the compound of the formula V and 4-amino-diphenyl ether is used as the compound of the formula VI in process 3 b for the preparation of the new thiadiazinones of the formula II, the process can be represented by the following equation:

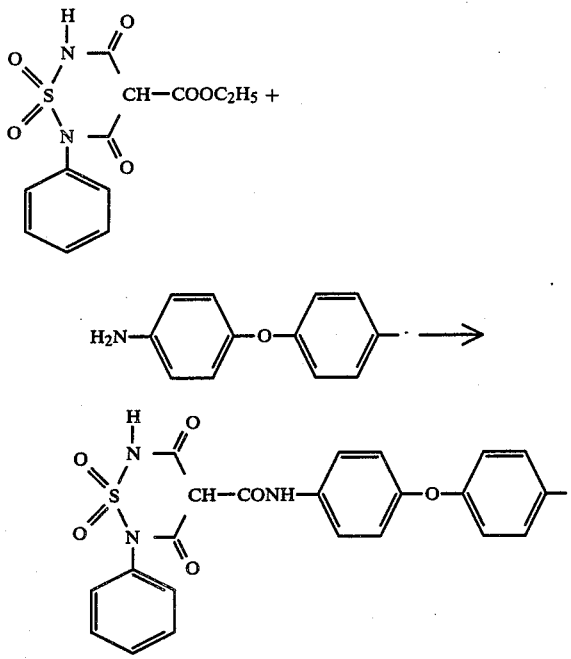

Compounds of the formula V in which the substituents $R^2$ and $R^3$ have the meanings given as preferred and particularly preferred in the case of the compounds of the formula I and $R^8$ represents methyl, ethyl or benzyl are preferably used. The following compounds of the formula V may be mentioned specifically: 2,6-dimethyl-4-ethoxycarbonyl-3,5-dioxo-2-H-3,4,5,6-tetrahydro-1,2,6-thiadiazine 1,1-dioxide, 2-methyl-6-isopropyl-3,5-dioxo-4-methoxycarbonyl-2-H-3,4,5,6-tetrahydro1,2,6-thiadiazine 1,1-dioxide, 2-ethyl-6-cyclohexyl-3,5-dioxo-4-ethoxycarbonyl-2-H-3,4,5,6-tetrahydro-1,2,6-thiadiazine 1,1-dioxide, 2-methyl-6-phenyl-3,5-dioxo-4-methoxycarbonyl-2-H-3,4,5,6-tetrahydro-1,2,6-thiadiazine 1,1-dioxide, 2-methyl-6-(4-chlorophenyl)-3,5-dioxo-4-ethoxycarbonyl-2-H-3,4,5,6-tetrahydro-1,2,6thiadiazine 1,1-dioxide and 2,6-diisopropyl-3,5-dioxo-4-benzyloxycarbonyl-2-H-3,4,5,6-tetrahydro-1,2,6-thiadiazine 1,1-dioxide.

The compounds of the formula VI are known or can be prepared by processes analogous to known processes.

The amines of the formula VI are known or can be prepared by processes analogous to known processes.

Amines of the formula VI in which the substituents $R^4$ and $R^5$ have the preferred and particularly preferred meanings given in the case of the compounds of the formula I are preferably used.

The following compounds of the formula VI may be mentioned specifically: 3-chloro-4-trifluoromethylaniline, 4-trifluoromethylmercaptoaniline, 3-chloro-4-trifluoromethylmercaptoaniline, 3-nitro-4-trifluoromethylaniline, 2,6-dichloro-4-trifluoromethylmercaptoaniline, 4-amino-4'-trifluoromethyldiphenyl ether and 4-amino-3'-trifluoromethyldiphenyl ether;

The reaction of the compounds of the formula V and VI is preferably carried out in the presence of diluents and in the presence of bases.

Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and moreover ketones, such as acetone, methyl ethyl ketone, methyl isopropyl ketone and methyl isobutyl ketone, and in addition esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethylsulphoxide, tetramethylene sulphone and hexamethylphosphoric acid triamide, and furthermore alcohols, such as methanol, ethanol, propanol and butanol.

Bases which may be mentioned are alkali metal and alkaline earth metal hydroxides and alkali metal and alkaline earth metal alcoholates, in particular sodium methylate or ethylate.

The reaction is carried out between 50° and 150° C., preferably between 60° and 110° C. It is preferably carried out under normal pressure.

The compounds of the formulae V and VI are employed in equimolar amounts, and a slight excess of one or other of the components provides no substantial advantages.

Working up is effected in a manner which is known per se, for example by adding water to the reaction mixture, separating off the organic phase and distilling off the solvent.

The active compounds according to the invention have a broad action against endoparasites. They have an action above all against cestodes, trematodes and nematodes, in particular liver fluke and gastric and intestinal nematodes in ruminants. They moreover also have an action against those gastric and intestinal nematodes which are resistant to the usual benzimidazole anthelmintics and therefore can no longer be treated adequately.

The action has been tested in an animal experiment following oral, parenteral and dermal administration to experimental animals heavily infested with parasites. The dosages used were tolerated very well by the experimental animals.

The active compounds according to the invention can be used as anthelmintics both in human and in veterinary medicine.

The active compounds according to the invention can be administered together with other customary anthelmintics.

The active compounds according to the invention can be used either as such or in combination with pharmaceutically acceptable excipients. Possible presentation forms in combination with various inert excipients are tablets, capsules, granules, aqueous suspensions, injectable solutions, emulsions and suspensions, elixirs, syrup, pastes and the like. Such excipients include solid diluents or fillers, a sterile aqueous medium and various non-toxic organic solvents and the like. The tablets and the like suitable for oral administration can of course be given a sweetener additive and the like. The therapeutically active compound in the abovementioned case should be present in a concentration of about 0.5 to 90% by weight of the total mixture, that is to say in amounts which are sufficient to achieve the abovementioned dosage range.

The formulations are prepared in a known manner, for example by extending the active compounds with solvents and/or excipients, if appropriate using emulsifying agents and/or dispersing agents, and, for example, in the case of the use of water as the diluent, organic solvents can be used as auxiliary solvents if appropriate.

Examples of auxiliaries which may be mentioned are: water, non-toxic organic solvents, such as paraffins (for example petroleum fractions), vegetable oils (for example groundnut (sesame) oil), alcohols (for example ethyl alcohol or glycerol), glycols (for example propylene glycol or polyethylene glycol) and water; solid excipients, such as, for example, natural rock powders (for example kaolins, aluminas, talc or chalk), synthetic rock powders (for example highly disperse silicic acid or silicates), sugars (for example sucrose, lactose and glucose); emulsifying agents, such as nonionic and anionic emulsifiers (for example polyoxyethylene fatty acid esters, polyoxyethylene fatty alcohol ethers, alkylsulphonates and arylsulphonates), dispersing agents (for example methylcellulose, starch and polyvinylpyrrolidone) and lubricants (for example magnesium stearate, talc, stearic acid and sodium lauryl-sulphate).

In the case of oral use, the tablets can of course also contain, in addition to the excipients mentioned, additives, such as sodium citrate, calcium carbonate and dicalcium phosphate, together with various adjuvants, such as starch, preferably potato starch, gelatin and the like. Lubricants, such as magnesium stearate, sodium lauryl-sulphate and talc, can furthermore also be used for tablet-making.

In the case of aqueous suspensions and/or elixirs intended for oral use, various flavour improvers or dyestuffs can be added to the active compounds, in addition to the abovementioned auxiliaries.

In the case of parenteral use, solutions, dragees, ampoules and the like can also be in the form of dosage units, each dosage unit being adapted such that it provides an individual dose of the active constituent.

The active compounds according to the invention can also be present in the formulations in mixtures with other known active compounds used in veterinary and/or human medicine for the treatment of infections and/or diseases, in particular L-2,3,5,6-tetrahydro-6-phenylimidazothiazole, benzimidazole carbamates, praziquantel or febantel.

The active compounds can be used in the customary manner. Administration is preferably oral, and parenteral administration, in particular subcutaneous, and also dermal application (pour-on or spot-on) are possible.

In general, it has proved advantageous to administer amounts of about 1 to about 100 mg of the active compounds per kg of body weight per day in order to achieve effective results.

Nevertheless, it may be necessary to deviate from the amounts mentioned, and in particular to do so as a function of the body weight of the experimental animal or of the nature of the administration route, but also on the basis of the animal species and its individual behaviour towards the medicament or the nature of its formulation and the time or interval at which administration takes place. Thus it can in some cases suffice to manage with less than the abovementioned minimum amount, whereas in other cases the upper limit mentioned must be exceeded. Where relatively large amounts are administered, it may be advisable to distribute these into several individual doses over the course of the day. The same dosage range is envisaged for administration in veterinary medicine. The other statements above also apply accordingly.

EXAMPLE A

In vitro nematode test
*Caenorhabditis elegans*

The active compound was dissolved in water or dimethyl sulphoxide (DMSO) and the solution was diluted with water to the desired use concentration. 0.01 ml of this solution was introduced onto a replica plate. 2 ml of an *E. coli* suspension into which 10–20 female animals or larvae of *Caenorhabditis elegans* in 0.5 ml of sterile M9 buffer solution had been introduced were added. The *E. coli* suspension was prepared by adding 1.8 l of sterile M9 buffer solution to 300 ml of an overnight culture of a uracil-dependent *E. coli* strain.

The test batch was incubated at 22° C. for 7 days and then evaluated. The extent to which the active compound impaired the multiplication was evaluated and the concentration at which the multiplication is prevented was stated. All the compounds of the preparation example thereby exhibited 100% activity when used in a concentration of 100 mg/l

EXAMPLE B

In vivo nematode test
*Heterakis spumosa*

Mice experimentally infected with *Heterakis spumosa* were treated orally by means of a stomach tube on four successive days 32 days after the infection. The animals are sacrificed 39 days after the infection and the number of parasites is determined. The active compound concentration at which at least 95% of the parasites have been killed (effective dose) is stated:

| Active compound Example No. | Effective dose mg/kg |
|---|---|
| 22 | 250 |
| 1 | 100 |
| 3 | 100 |
| 20 | 10 |
| 32 | 25 |

EXAMPLE C

In vivo cestode test
*Hymenolepis nana*

Mice experimentally infected with *Hymenolepis nana* were treated orally by means of a stomach tube on four successive days 10 days after the infection. The animals are sacrificed 17 days after the infection and the number of parasites is determined. The active compound concentration at which at least 95% of the parasites have been killed (effective dose) is stated:

| Active compound Example No. | Effective dose mg/kg |
|---|---|
| 1 | 250 |
| 3 | 100 |
| 18 | 50 |

EXAMPLE D

In vivo nematode test
*Strongyloides ratti*

Rats experimentally infected with *Stongyloides ratti* were treated orally by means of a stomach tube on three successive days 7 days after the infection. The animals are sacrificed 13 days after the infection and the number of parasites is determined. The active compound concentration at which at least 95% of the parasites have been killed (effective dose) is stated:

| Active compound Example No. | Effective dose mg/kg |
| --- | --- |
| 4 | 100 |
| 14 | 100 |
| 28 | 100 |
| 18 | 250 |
| 35 | 25 |
| 33 | 5 |

EXAMPLE E

*Haemonchus contortus*/sheep

Sheep experimentally infected with *Haemonchus contortus* were treated after the end of the pre-patency time of the parasites. The active compounds were administered orally as pure active compound in gelatin capsules.

The degree of effectiveness is determined by quantitatively counting the worm eggs excreted with the faeces, before and after treatment.

Complete cessation of the excretion of eggs after treatment means that the worms have been expelled or are so severely damaged that they can no longer produce any eggs (effective dose).

The active compounds tested and the effective dosages can be seen from the following table:

| Active compound Example No. | Effective dose in mg/kg |
| --- | --- |
| 25 | 5 |
| 26 | 2,5 |
| 28 | 5 |
| 33 | 5 |
| 21 | 10 |
| 20 | 10 |
| 31 | 2,5 |
| 32 | 2,5 |
| 35 | 5 |

PREPARATION EXAMPLES (a) General instructions for the preparation of the thiadiazinones according to process 3a)

In each case 0.03 mol of the thiadiazinone of the formula III and of the isocyanate are taken as a solution in 120 ml of dry tetrahydrofuran and a solution of 0.03 mol (4.56 g) of "DBU" in 30 ml of tetrahydrofuran are added at room temperature in the course of 30 minutes. The initially pale brown solution becomes dark and slight evolution of heat occurs, so that the internal temperature must be kept below 25° C. by cooling with water. The mixture is then subsequently stirred at room temperature until conversion is complete (about 4–5 hours, thin layer chromatography sample!). The entire batch is then evaporated, the residue is taken up in 100 ml of methylene chloride and the mixture is stirred with 100 ml of dilute hydrochloric acid (10% strength). The organic phase is separated off, washed neutral with aqueous sodium bicarbonate solution and dried over sodium sulphate. After the solvent has been removed on a rotary evaporator, the residue is recrystallized from ligroin or isopropanol or chromatographed.

The active compounds of the following examples are obtained analogously:

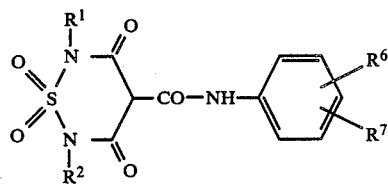

| Example | $R^1$ | $R^2$ | $R^6$ | $R^7$ | Melting point |
| --- | --- | --- | --- | --- | --- |
| 1 | $CH_3$ | $iC_3H_7$ | 3-Cl | H | 119° |
| 2 | $CH_3$ | $iC_3H_7$ | 3-$CF_3$ | H | 92–93° |
| 3 | $CH_3$ | $iC_3H_7$ | 4(3'-$OC_6H_4CF_3$) | H | 116–117° |
| 4 | $CH_3$ | $iC_3H_7$ | 4-$SCF_3$ | H | 107–109° |
| 5 | $CH_3$ | $iC_3H_7$ | 4(4'-$OC_6H_4CF$)$_3$ | H | 98–99° |
| 6 | $C_2H_5$ | cyclohexyl | 4-$SCF_3$ | H | 98–100° |
| 7 | $C_2H_5$ | cyclohexyl | 3-Cl | H | 128–129° |
| 8 | $C_2H_5$ | cyclohexyl | 4-$CF_3$ | H | 128–129° |

-continued

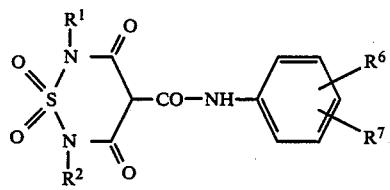

| Example | R¹ | R² | R⁶ | R⁷ | Melting point |
|---|---|---|---|---|---|
| 9 | $C_2H_5$ | cyclohexyl-H | 4-$SCF_3$ | 3-Cl | amorphous |
| 10 | $C_2H_5$ | cyclohexyl-H | 4-$OCF_3$ | 3-Cl | oil |
| 11 | $CH_3$ | $C_6H_5$ | 3-Cl | H | 172–173° |
| 12 | $CH_3$ | $C_6H_5$ | 3-$CF_3$ | H | 143° |
| 13 | $CH_3$ | $C_6H_5$ | 4-$SCF_3$ | H | 211° |
| 14 | $CH_3$ | $C_6H_5$ | 4(3'-$OC_6H_4OCF_3$) | H | 164° |
| 15 | $CH_3$ | $C_6H_5$ | 4-$OCF_3$ | H | 165–8° |
| 16 | $CH_3$ | 4Cl$C_6H_4$ | 3-Cl | H | 163° |
| 17 | $CH_3$ | 4Cl$C_6H_4$ | 3-$CF_3$ | H | 156° |
| 18 | $CH_3$ | 4Cl$C_6H_4$ | 4-$SCF_3$ | H | 207° |
| 19 | $CH_3$ | 4Cl$C_6H_4$ | 4-($OC_6H_4$3-$CF_3$) | H | 151° |
| 20 | $CH_3$ | 4Cl$C_6H_4$ | 4-$CF_3$ | H | 163° |
| 21 | $CH_3$ | 4Cl$C_6H_4$ | 4-$OCF_3$ | H | 174° |
| 22 | $CH_3$ | Ph | 4-$CF_3$ | H | 225° |
| 23 | $CH_3$ | $CH_3$ | 3-Cl | H | 174–175° |
| 24 | $CH_3$ | $CH_3$ | 3-$CF_3$ | H | 139–140° |
| 25 | $CH_3$ | $CH_3$ | 4-$CF_3$ | H | 145–146° |
| 26 | $CH_3$ | $CH_3$ | 4-$OCF_3$ | H | 112° |
| 27 | $CH_3$ | $CH_3$ | 4-$SCF_3$ | H | 111° |
| 28 | $CH_3$ | $CH_3$ | 4-O-C₆H₄-3-$CF_3$ | H | 132° |
| 29 | $CH_3$ | $C_2H_5$ | 3-Cl | H | 159–160° |
| 30 | $CH_3$ | $C_2H_5$ | 3-$CF_3$ | H | 104–105° |
| 31 | $CH_3$ | $C_2H_5$ | 4-$CF_3$ | H | 79–80° |
| 32 | $CH_3$ | $C_2H_5$ | 4-$OCF_3$ | H | 77° |
| 33 | $CH_3$ | $C_2H_5$ | 4-O-C₆H₄-4-$CF_3$ | H | 76–78° |
| 34 | $CH_3$ | $C_2H_5$ | 4-$SCF_3$ | H | 110–111° |
| 35 | $CH_3$ | $CH_3$ | 4-O-C₆H₄-4-$CF_3$ | H | 144–146° |
| 36 | $CH_3$ | $C_2H_5$ | 4-O-C₆H₄-3-$CF_3$ | H | 97–98° |

We claim:
1. A method of combating endoparasites which comprises applying to such endoparasites or to an endoparasite habitat an endoparasiticidally effective amount of a thiadiazionone of the formula

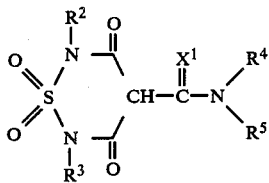

in which

X$^1$ is O or S,

R$^2$ and R$^3$ each independently is hydrogen, C$_{1}$–C$_{4}$-alkyl, C$_{3-8}$-cycloalkyl, phenyl or benzyl, R$^4$ is hydrogen or C$_{1-4}$-alkyl, and R$^5$ is phenyl or phenyl substituted by at least one member independently selected from the group consisting of C$_{1-4}$-alkyl, C$_{1-4}$-alkoxy, C$_{1-4}$-alkylthio, C$_{1-4}$-haloalkyl, C$_{1-4}$-haloalkoxy, C$_{1-4}$-haloalkylthio, C$_{1-2}$-alkylenedioxy, C$_{1-2}$-haloalkylenedioxy, hydroxy, halo, cyano, nitro, amino, C$_{1-4}$-monoalkylamino and -dialkylamino, formyl, carboxyl, C$_{1-4}$-carbalkoxy, sulpho, C$_{1-4}$-alkylsulphonyl, phenylsulphonyl, naphthylsulphonyl, phenyl, naphthyl, phenoxy, naphthoxy, phenylthio, pyridyloxy, and phenyl, naphthyl, phenoxy, naphthoxy, phenylthio or pyridyloxy substituted by CF$_3$ or OCF$_3$.

2. The method according to claim 1 in which

R$^2$ and R$^3$ each independently is C$_{1-4}$-alkyl, cyclohexyl, phenyl, halophenyl or benzyl, and R$^5$ is phenyl, or phenyl substituted by at least one member independently selected from the group consisting of C$_{1-4}$-alkyl, C$_{1-4}$-alkoxy, C$_{1-4}$-haloalkoxy, C$_{1-4}$-haloalkylthio, C$_{1-4}$-alkylthio, halosulphonyl, C$_{1-4}$-alkylsulphonyl, C$_{1-4}$-haloalkylsulphonyl, C$_{1-4}$-haloalkyl, methylenedioxy, halomethylenedioxy, ethylenedioxy, haloethylenedioxy, halo, NO$_2$, phenyoxy and pyridyloxy.

3. The method according to claim 1, in which

R$^2$ and R$^3$ each independently is methyl, ethyl, cyclohexyl, phenyl or chlorophenyl, R$^4$ is hydrogen, and R$^5$ is phenyl, or phenyl substituted by at least one member independently selected from the group consisting of chlorine, NO$_2$, CF$_3$, OCF$_3$, SO$_2$F, SCF$_3$, SCF$_2$Cl, SOCF$_3$, SO$_2$CF$_3$, OCH$_3$, OCF$_2$CF$_2$H, phenoxy, pyridyloxy, or phenoxy or pyridyloxy substituted by CF$_3$ or OCF$_3$.

4. A thiadiazinone of the formula

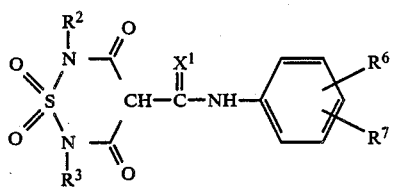

in which

X$^1$ is O or S,

R$^2$ and R$^3$ each is hydrogen, C$_1$–C$_4$-alkyl, C$_{3-8}$-cycloalkyl, phenyl or benzyl, R$^6$ is SCF$_3$, phenoxy or pyridyloxy, and R$^7$ is hydrogen or halogen.

5. An endoparasiticidal composition comprising an endoparasiticidally effective amount of a compound according to claim 4 and a diluent.

6. A method of combating endoparasites which comprises applying to such endoparasites or to an endoparasite habitat an endoparasiticidally effective amount of a thiadiazinone according to claim 4.

* * * * *